United States Patent [19]

Krenn et al.

[11] Patent Number: 4,611,487
[45] Date of Patent: Sep. 16, 1986

[54] MICRO HARDNESS TESTING DEVICE

[75] Inventors: Manfred Krenn, Feldkirchen; Gerhard Raffer, Graz; Alfred Wagendristel, Perchtoldsdorf; Herwig Bangert, Vienna, all of Austria

[73] Assignees: Anton Paar, KG, Graz; Herwig Bangert, Vienna; Alfred Wagendristel, Perchtoldsdorf, all of Austria

[21] Appl. No.: 711,889

[22] Filed: Mar. 15, 1985

[30] Foreign Application Priority Data

Mar. 16, 1984 [AT] Austria ................................ 894/84

[51] Int. Cl.$^4$ .................................................. G01N 3/42
[52] U.S. Cl. ............................................................ 73/81
[58] Field of Search .......................... 73/78, 81, 82, 806

[56] References Cited

U.S. PATENT DOCUMENTS

| 2,803,130 | 8/1957 | Bernhardt | 73/81 |
|---|---|---|---|
| 3,693,417 | 9/1972 | Fritz et al. | 73/81 |
| 3,822,946 | 7/1974 | Rynkowski | 73/81 |
| 4,019,376 | 4/1977 | Iwasaki | 73/81 |
| 4,094,188 | 6/1978 | Bellouin et al. | 73/81 |
| 4,111,039 | 9/1978 | Yamawaki et al. | 73/81 |
| 4,132,224 | 1/1979 | Randolph | 73/81 |
| 4,304,123 | 12/1981 | Aschinger et al. | 73/81 |
| 4,450,713 | 5/1984 | Arimatsu | 73/81 |

FOREIGN PATENT DOCUMENTS 1040382  9/1983  U.S.S.R. ................................ 73/81

Primary Examiner—Stewart J. Levy
Assistant Examiner—Robert R. Raevis
Attorney, Agent, or Firm—Beveridge, DeGrandi & Weilacher

[57] ABSTRACT

A micro hardness testing device (durometer) comprises a permanent magnet having a plunger. A spring arrangement has at least one strain gauge that provides a signal on bending of the spring arrangement. The spring arrangement is carried by the plunger. A penetration body is loadable via the spring arrangement, and the plunger is connected to a current supply. The strain gauge signal is converted to an electrical signal as a measuring signal for the force applied to the penetration body. The measuring signal is supplied to an evaluation unit. The plunger, the permanent magnet and the spring arrangement are enclosed by a housing adapted for insertion into a revolvable nose piece of a microscope. The housing approximates the shape and dimensions of an objective insert for the microscope. The penetration body is adjustable in an optical axis of the microscope.

24 Claims, 4 Drawing Figures

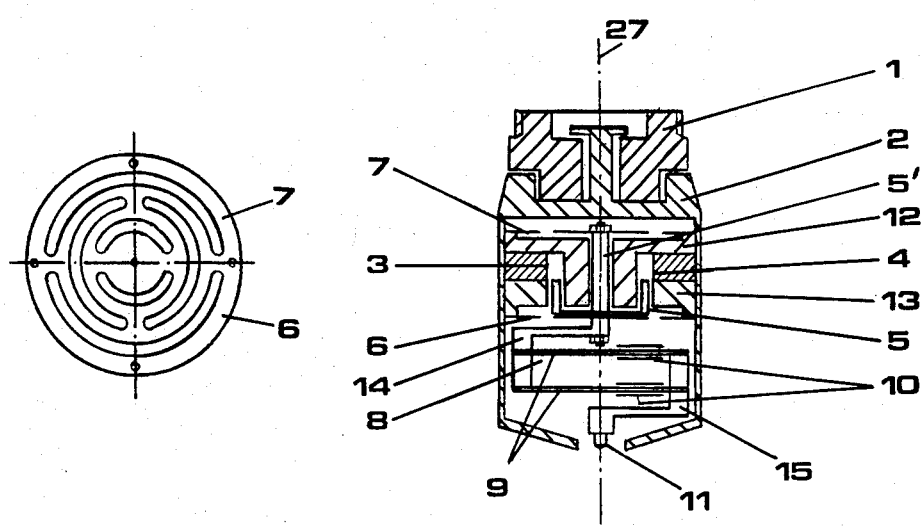
FIG. 1a
FIG. 1
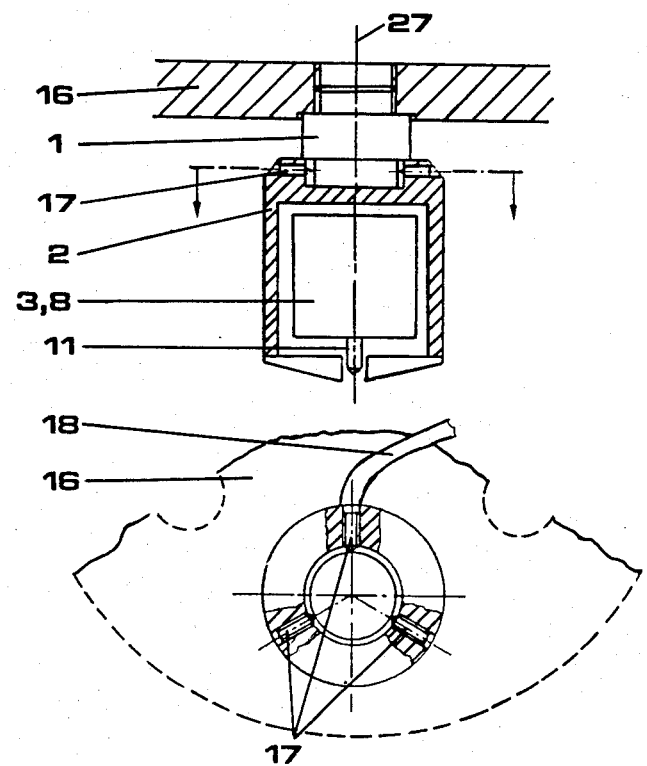
FIG. 2

MICRO HARDNESS TESTING DEVICE

The invention relates to a micro hardness testing device (durometer) having a penetration body loadable via a spring arrangement carrying at least one, preferably two to four, optionally opposed strain gauges, with the signals of the strain gauges on bending of the spring arrangement being converted to electrical signals as a measuring signal for the force applied to the penetration body and supplied to a control or evaluation unit and the spring arrangement being carried by the plunger (moving coil) of a permanent magnet system.

It is the object of the invention to provide a precise and optionally automatically operating micro hardness testing device as an add-on unit for light-optical microscopes.

This is achieved in a micro hardness testing device of the type initially mentioned by providing that the plunger, the permanent magnet system and the spring arrangement as well as, optionally, the penetration body in its inactive position, are enclosed by a housing insertable or screwable into the revolving objective changer or nose piece of a microscope or approaching the shape and dimensions of an objective insert, with the penetration body adjustable in the optical axis optionally forming the axis of symmetry of the housing. It is preferable that the control unit be provided with a preselection means for adjusting the approaching rate of the penetration body to a sample or for regulating the power supply of the plunger, with input stores for various power increase rates associated with the control unit. By means of a micro hardness testing device constructed this way, it is possible to carry out hardness tests in a light optical microscope in a simple manner. No transfer of the sample between hardness tester and microscope and no tedious search for the impression on the sample surface is necessary; the imprint appears in the center of the field of view. For space saving, it is of advantage if the spring arrangement disposed between the plunger and the penetration body extends essentially transversely to the optical axis and is formed of at least one leaf spring. One end of the spring arrangement is preferably attached to the plunger or connected to it via a transition piece and the other end of the spring arrangement carries the penetration body directly or via a transition piece. It is of advantage if the ends of the parallel leaf springs laterally project beyond the plunger, the transition piece attached to the plunger protrudes laterally and the transition piece carrying the penetration body is directed towards the center of the housing.

For the precise guidance of the plunger, it is provided that the plunger is displaceable in relation to the permanent magnet system and is attached and thus guided in axial direction by two spring plates or membranes which are superposed in the housing, perforated and fixed on their peripheries. For adjusting purposes, it is practical to provide for the housing to be carried by a threaded piece for screwing into a revolving objective changer and to be adjustable or laterally displaceable on this threaded piece by means of, e.g., adjusting screws.

The invention is explained in detail with reference to the accompanying drawing.

FIG. 1 shows a sectional view of a micro hardness tester head;

FIG. 1a shows a plan view of supporting springs;

FIG. 2 shows a schematic view of the micro hardness testing device and

Figure 3:
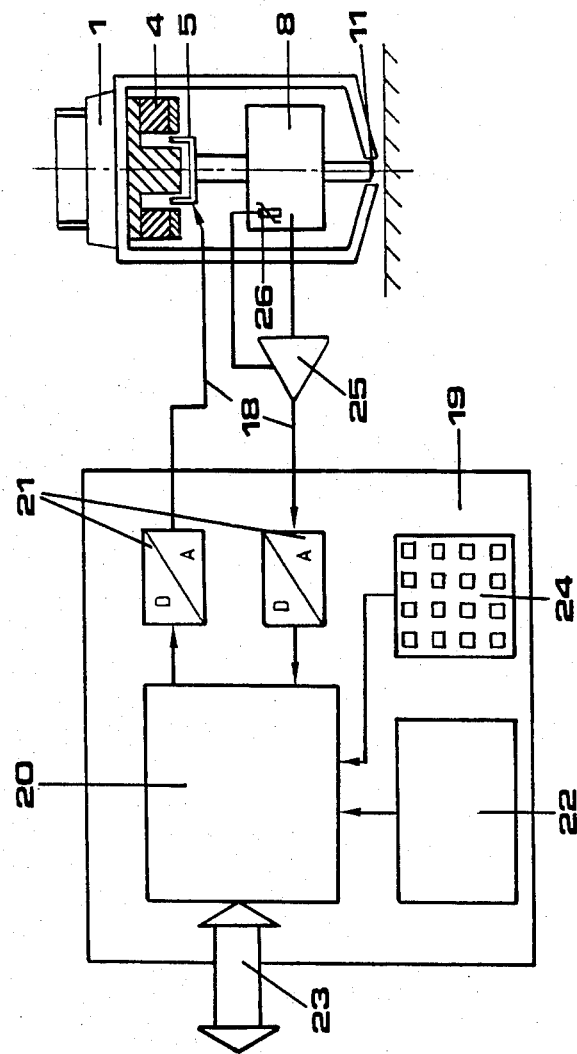
FIG. 3 shows a schematic connection diagram.

In the construction of the micro hardness tester or ultra micro hardness tester for a light-optical microscope according to the invention; the following points are essential: the tester or the penetration means should have the outer dimensions of a standard objective and should be independent of the assembling position. The micro hardness tester should further be operable by means of a computer or via an evaluation and control unit via a serial interface so that it can be assembled into an automatic measuring set-up.

The micro hardness testing head shown in sectional view in FIG. 1 has the form of an objective and is provided with a threaded piece 1 (for screwing into a revolving nose piece) and a housing 2. In the housing, there is a plunger magnet system 3 for power generation and a dynamometer unit 8 carrying a penetration body 11.

The housing together with the penetration body 11, the plunger magnet system 3 and the dynamometer unit 8 is adjustable in relation to the threaded piece 1 by three screws 17. Untightening one screw 17 and tightening the other two screws 17 moves the housing and thus the penetration body 11 in the direction of the untightened screw, thus permitting the centering of the penetration body 11 to the optical axis of the light-optical microscope.

The plunger magnet system 3 consists of an annular permanent magnet 4 containing rare-earth elements, a pole core of soft iron and a pole plate of soft iron. A cylindrical ring shaped plunger or moving coil 5 is disposed in the homogenous magnetic field between the pole core 12 and the pole plate 13. The exact guidance of the plunger 5 in axial direction or its orientation in the optical axis and thus the guidance of the dynamometer unit 8 with the penetration body 11 is assured by one each spring membrane 6,7 positioned above and below the plunger 5 and preventing lateral movement. The spring membranes 6,7 are shown in FIG. 1a. In the center of each one of them the plunger 5 or a supporting element 5' extending it are attached or screwed to the spring membranes. The outer ring of the spring membrane 7 is attached to the pole core 12, the outer ring of the spring membrane 6 is attached to the pole plate 13.

The dynamometer unit 8 consists of a double spring arm 9 provided with a glued-on strain gauge 10 for measuring the spring bending and thus the penetration force. Force application, force measurement and penetration body 11 are positioned in one axis (axis of motion). The construction of the dynamometer 8 as a double spring arm 9 prevents a tilting or displacement of the penetration body during the penetrating operation.

The penetration force is generated via the current-carrying plunger 5 in a highly homogenous magnetic field of the permanent magnet systems (12, 4, 13). The dynamometer unit 8 permitting constant control of the force during the penetration operation is disposed between the plunger 5 and the diamond point of the penetration body 11.

Force measuring is effected via the bending of the double spring arm 9 by means of the strain gauge 10. This depends on the spring arm geometry chosen and on the modulus of elasticity of the selected spring material. The modulus of elasticity (Young's modulus) has a temperature coefficient which can be taken into account or compensated for by measuring the spring temperature. This purpose is served by a thermistor 26 shown in FIG. 3 next to the double spring arm 9, its signal is transmitted to a pre-amplifier 25 for the output signal of the strain gauge 10 or the differential signal of strain gauges 10 disposed in bridge circuit. The output signals of the strain gauges 10 are amplified as a function of the temperature of the double spring arm 9, so that temperature compensation becomes possible.

In its active position the penetration body 11 remains protected in the housing 2 so that the point will be protected against damage.

The plunger 5 or its supporting rod 5' carries a transition piece 14 (FIG. 1), which protrudes laterally and carries the end of the double spring arrangement 9. A further transition piece 15 pointing backward into the center of the housing 2 and carrying the penetration body is provided on the other end of the spring arrangement 9.

The permanent magnet system 12, 4, 13 can be provided with several permanent magnets. The plunger 5 can be square or rectangular, although a cylindrical or cylindrical ring shaped coil preferably not having a core is preferred. The dynamometer unit 8 can consist of only one spring or leaf spring, although in order to prevent the tilting of the penetration body 11, the provision of two parallel leaf springs whose ends are fixed in the transition pieces 14, 15 is preferable.

The transition pieces 14, 15 are built as rigidly as possible.

It is possible to glue one each or, for increased measuring precision, several strain gauges 12 onto the leaf springs 9 of the dynamometer unit 8.

It is further possible to provide a permanently magnetic solenoid plunger instead of the plunger 5 and to replace the permanent magnet 4 by an excitation coil wound on a soft iron core (ring). In this case, movement of the solenoid plunger is effected by current supply to the coil system.

In mounting and adjusting the hardness testing head on the microscope, the threaded piece 1 is screwed into the revolving nose piece 16 (preferably next to the objective "100x"). The next and—if required—the next but one place next to the hardness testing head is (are) temporarily cleared in order to make room for an adjustment of the diamond point or the penetration body 11 into the optical axis 27 of the microscope (FIG. 2). The housing 2 is adjustably positioned on the threaded part 1 by means of adjusting screws 17 distributed over the periphery and can be centered therewith.

It can be centered in respect to the optical axis 27 by successive unscrewing of one screw and tightening of the other two screws 17. The signals from the strain gauges 10—equivalent to the actual force applied to the indentor or penetration body—are transmitted to the evaluation unit.

The dynamometer 8, the control and calculating unit 20 and the plunger coil 5 form a closed loop. The signal from the dynamometer 8 is compared with a reference signal which corresponds to the preselected force and which is generated in the control and calculating unit 20. As long as there is any difference in the two signals, the current through the plunger coil is altered such that the difference between the signal from the dynamometer 8 and the reference signal is reduced.

The control and calculating unit 20 contains a microprocessor; the microprocessor is connected to the plunger 5 or the strain gauges 10 via a digital-to-analog converter or analog-to-digital converter 21. Inputting of parameters is effected via a keyboard 24 or a serial interface 23. Measuring values and functions and/or results are presented on an alphameric display 22 (FIG. 3).

The evaluation unit 19 permits the preselection of the measuring parameters, such as testing force, penetration period and force increase rate, by inputting to the control unit 20 via a keyboard 24 or via a serial interface.

By supplying current to the plunger 5, the dynamometer unit 8 with the penetration body 11 approaches the surface of the sample. The current increase and thus the approaching rate of the penetration body 11 is determined for the purpose of adjustment of the impacting force to the testing force (low testing force calls for low approaching rate) according to input or predetermined values. The contact of the penetration body 11 with the sample is detected by the control unit by the first appearance of a signal from the strain gauges 10, which corresponds to a force applied to the penetration body 11.

On recording this very first signal, there is a stop of further approach by keeping the coil current constant for one or two seconds in order to distinguish between signals indicating actual force on the penetration body and signals coming from other causes, such as drifting, vibrations and the like.

After contact, the penetration body 11 penetrates into the sample with defined force increase rate. The testing force is constantly measured and regulated to the preselected value without overshooting. The testing force is then kept constant during the measuring period and after the testing operation, the penetration point 11 is returned to the safe inactive position.

The hardness testing head has the shape of an objective and can thus be used in any conventional precision microscope, its function is assured in any given assembling position. The construction of the double spring arm 9 prevents a tilting or drifting of the penetration body 11 during the penetration process and permits a determination of the testing force with high resolution and precision. The measuring range extends from 0.05 mN to 2N and thus covers the entire micro hardness and ultra micro hardness range. Assembling of the hardness testing head into an automatic measuring set-up is possible due to the external possibility of preselecting the measuring parameters (serial interface 23) thus a closed control loop during measuring is formed with a defined penetration operation (e.g. linear increase of the testing force) and an exact keeping constant of the testing force during the period of penetration.

At the end of the testing operation, the diagonal of the square impression in the sample is measured e.g. by an ocular micrometer and the data are input into the evaluation unit 19 in which calculation of the hardness is effected in the desired units according to the formulae defining Vickers or Knoop hardness in the known manner.

We claim:

1. Micro hardness testing device (durometer) comprising
permanent magnet means having a plunger;
spring arrangement means having at least one strain gauge that provides a signal on bending of the spring arrangement, wherein the spring arrangement is carried by the plunger;
a penetration body loadable via the spring arrangement means;
means for connecting the plunger to a current supply;

means for converting the strain gauge signal to an electrical signal as a measuring signal for force applied to the penetration body;

means for supplying the measuring signal to an evaluation unit;

wherein the plunger, the permanent magnet means and spring arrangement means are enclosed by a housing adapted for insertion into a revolvable nose piece of a microscope;

and wherein the housing approximates shape and dimensions of an objective insert for the microscope;

and further wherein the penetration body is adjustable in an optical axis of a microscope.

2. Device according to claim 1, wherein the housing is screwable into the nose piece of a microscope.

3. Device according to claim 1, wherein the spring arrangement means is disposed between the plunger and the penetration body, the spring arrangement extends essentially transversely to the optical axis, and the spring arrangement is formed of at least one leaf spring.

4. Device according to claim 1, wherein the spring arrangement means has an end connected to the plunger via a transition piece.

5. Device according to claim 1, wherein the spring arrangement comprises two parallel leaf springs and the leaf springs have respective ends that are fixed in rigid transition pieces, wherein one transition piece is fixed to the plunger and the other transition piece carries the penetration body.

6. Device according to claim 5, wherein the ends of said parallel leaf springs laterally project beyond the plunger, the transition piece attached to the plunger protrudes laterally and the transition piece carrying the penetration body is directed towards the center of the housing.

7. Device according to claim 1, wherein the plunger is arranged symmetrically in relation to the optical axis.

8. Device according to claim 1, wherein the plunger is displaceable in relation to the permanent magnet means, and the plunger is attached to and guided in axial direction by two perforated spring membranes, which are superposed in the housing and fixed along their peripheries on the housing.

9. Device according to claim 1, wherein the housing is carried by a threaded piece for screwing into a revolvable nose piece of a microscope and is laterally displaceable on said threaded piece by adjusting means.

10. Device according to claim 9, wherein the adjusting means comprise adjusting screws in the housing.

11. Device according to claim 1, wherein the plunger is annular and is surrounded by the permanent magnet means.

12. Device according to claim 1, wherein the evaluation unit comprises a control and calculating unit having a comparator to which the signal of the strain gauge and a predetermined set-point value of force are conveyed for comparison, and a plunger control means is disposed in the current supply of the plunger for adjustment of the current supply to the plunger as a function of the comparison between the strain gauge signal and the set-point value of force.

13. Device according to claim 12, wherein said control and calculating unit responds to a sudden increase in testing force and monitors first arrival of measuring signals and then stops the penetration body for a preselected time.

14. Device according to claim 12, wherein said control and calculating unit comprises a return circuit for controlling current supply to the plunger for returning the penetration body to an inactive position on expiration of a testing period.

15. Device according to claim 12, wherein output signals from the control and calculation unit are conveyed to a display means.

16. Device according to claim 12, wherein said control and calculating unit is provided with a preselection means containing input stores for adjustment of different approaching rates of the penetrtion body to a sample and for control of the current supply to the plunger.

17. Device according to claim 1, wherein a temperature measuring means is provided for the spring arrangement means, which measuring means is connected to a preamplifier of a compensating circuit in which the signal from the strain gauge is changeable depending upon the temperature of the spring arrangement.

18. Device according to claim 17, wherein the temperature measuring means is a thermistor.

19. Device according to claim 1, comprising
a monitoring unit for constant control of the measuring signals during a predetermined testing period and for keeping testing pressure constant, and
means for displaying testing force.

20. Device according to claim 1, wherein the housing is elongated and the housing has a longitudinal axis that is the axis of symmetry of the housing and coincides with an optical axis of a microscope.

21. Device according to claim 1, wherein the penetration body in an inactive position is enclosed in the housing.

22. Device according to claim 1, wherein the spring arrangement means is attached to the plunger.

23. Device according to claim 1, wherein the penetration body is carried directly by one end of the spring arrangement means.

24. Device according to claim 1, wherein the penetration body is carried indirectly via a transition piece by one end of the spring arrangement means.

* * * * *